United States Patent [19]

Haas et al.

[11] 4,060,602

[45] Nov. 29, 1977

[54] ORAL PREPARATIONS FOR PREVENTING DENTAL CARIES

[75] Inventors: Gerhard Julius Haas, Woodcliff Lake, N.J.; Edwin Bernard Herman, Yorktown Heights, N.Y.

[73] Assignee: General Foods Corporation, White Plains, N.Y.

[21] Appl. No.: 735,723

[22] Filed: Oct. 26, 1976

Related U.S. Application Data

[63] Continuation-in-part of Ser. No. 466,945, May 6, 1976, abandoned.

[51] Int. Cl.$^2$ .................... A61K 7/26; A61K 35/78
[52] U.S. Cl. ........................... 424/58; 424/195
[58] Field of Search .................. 424/58, 195

[56] References Cited

U.S. PATENT DOCUMENTS

| 1,107,389 | 8/1914 | Waller | 424/53 |
|---|---|---|---|
| 3,876,759 | 4/1975 | Pensak et al. | 424/58 |

OTHER PUBLICATIONS

Fenaroli's Handbook of Flavor Ingredients (1971) Chem. Rubber Co. Cleveland, Ohio pp. 177–178, 199–200.

N.A.S. Publ. 1274 (1965) Chemicals Used in Food Processing, pp. 207, 212–213, 247 Wash., D. C.
Steinmetz Codex Vegetabilis (1957) Amsterdam, Holland, pp. 3,7,8, entrie No. 836, No. 837.
Hocking (1955), A Dictionary of Terms in Pharmacognosy C. C. Thomas, Springfield, Ill. p. 171.
A.Ph.A. (1943), The Pharmaceutical Recipe Book 3rd ed. p. 400, Wash., D. C.
Gorgas (1884), Dental Medicine, J. A. Churchill, London England, pp. 21, 38.
Pereira (1854), The Elements of Materia Medica and Therapeutics 3rd ed. Blanchard & Lea, Phila., Pa. pp. 756–758.

*Primary Examiner*—Shep K. Rose
*Attorney, Agent, or Firm*—T. J. Carvis; D. J. Donovan; B. P. Struzzi

[57] ABSTRACT

This invention has identified two compositions, pimento berry oil and terpeneless bay oil, which are effective as antimicrobial agents against cariogenic streptoccus mutans and *Lactobaccilli casei* and fermenti. These active compositions, when employed in oral preparations and used in an effective regimen of repeated application to these bacteria in the mouth, are useful in reducing dental plaque and dental caries.

2 Claims, No Drawings

ORAL PREPARATIONS FOR PREVENTING DENTAL CARIES

BACKGROUND OF THE INVENTION

This application is a continuation-in-part of Ser. No. 466,945, filed May 6, 1974, now abandoned.

The underlying causes of dental caries are multifaceted. One aspect is the microbiological one. In order for caries to develop, infection by microorganisms has to occur.

During recent years it has been found that the organisms most often associated with the formation of multisurface caries are certain salivary streptococci belonging to the strep mutans group. Multi-surface caries is particularly prevalent in children and young adults; the so-called rampant caries belongs to this type. The cariogenic organisms appear to have the special capability of developing a high molecular weight, water-insoluble type of dextran from sucrose. This dextran is believed to be a major constituent of the dental plaque normally associated with dental caries.

Various means have been comtemplated for controlling the amount of plaque in the mouth. The use of certain enzymes such as Pancreatin is disclosed in U.S. Pat. No. 3,235,460 as effective to inhibit the formation of dental plaque. Commonly-assigned U.S. Pat. Nos. 3,932,603 and 3,940,476, and also U.S. Patent Application Ser. No. 126,465, filed March 15, 1971, now abandoned, disclose several surface active agents which are also effective to inhibit or reduce the formation of dental plaque.

It has also been proposed to employ direct bactericidal action on the cariogenic microorganisms to assist in the reduction or prevention of dental caries. U.S. Pat. Nos. 2,921,886 and 3,450,812 respectively disclose alkyl morpholine compounds and nitrogen based compounds having an empirical formula of $C_{38}H_{61}NO_{14}$ as antimicrobials which are effective as anticaries agents.

A number of aldehydes have been claimed as anticaries and anti-plaque agents when used in mouthwash or chewing gum.

Litchfield and Vely (U.S. Pat. No. 3,749,766) claim an anticaries chewing gum containing any of the following aldehydes at a level of 0.1% to 5.0%; n-hexaldehyde, 2-hexene-1-al, n-heptaldehyde, octanaldehyde, nonaldehyde, decanaldehyde, undecylic aldehyde, undecylenic aldehyde, lauric aldehyde, or methylnonyl acetaldehyde. These aldehydes were effective when incorporated in rat diets in 90 days feeding tests.

Litchfield and Vely (U.S. Pat. No. 3,651,206) claim an anticaries chewing gum containing glyceraldehyde at a level of 0.5% to 5.0%, gylcolaldehyde at a level of 0.5% to 2.0%, or pyruvaldehyde at a level of 0.1% to 2.0%. The authors found that upon being chewed, the majority of the cariostatic agents were liberated in 2½ minutes. Significant activity was also found in saliva obtained after 2½ additional minutes. It was, therefore, suggested that the gum be chewed from 2½ to 5 minutes for anticaries activity. Again in vivo tests involved 90 day feeding studies.

Eigen (U.S. Pat. No. 3,497,590) claims glutaraldehyde in a mouthwash at a level of 1.0% and in a tooth powder or dental cream, at a level of 0.25% is effective in preventing dental calculus formation and in reducing caries formation in the mouth. This substance was swabbed on rat teeth at a concentration of .01%, two times a day, for 30 seconds and was found to reduce calculus formation when this regimen was continued for one week.

In addition to antimicrobial agents, antibiotics also have been found to reduce the incidence of dental caries and/or buildup of dental plaque in experiments involving humans or animal subjects.

the antibiotic Vancomycin, applied to the teeth of human volunteers as an adhesive paste, once a day for eight days, in a dose of 3 mg, resulted in reduction in formation of dental plaque (Mitchell, D.F., and Holmes, L.A., 1965. Topical Antibiotic Control of Dentogingival Plaque. J. Periodont., 36: 202-208).

Antinobolin, another antibiotic, was found to be cariostatic in rats when fed in a dose of 37.6 PPM, over 22 days, as part of a cariogenic high sucrose diet (Keele, Bernard B. Jr., Powell, Hubert L. Jr., Navia, Juan, M., and McGhee, Jerry, 1971. Effects of Actinobolin on Growth and Some Metabolic Activities of Cariogenic Streptococci in vitro and in vivo, Appl. Microbiol. 22: 957-962).

Chlorhexidine is an antimicrobial agent which has been found to be effective in inhibiting both plaque and caries formation in rats and humans. Rats, fed a cariogenic high sucrose diet, were treated once a day for 15 seconds with a 0.125% solution of chlorhexidine diacetate or with phenylmercuric borate in a glycerol solution. After 20 days, a reduction in caries incidence was noted for animals treated with both disinfectants. Chlorohexidine diacetate was the more effective agent (Regolati, B., Konig, K. G., and Muhlemann, H. R. 1969. Effects of Topically applied Disinfectants on Caries in Fissures and Smooth Surface of Rat Molars. Helv. Odont. Acta 13: 28-31).

A group of human subjects, who rinsed their mouths ten times a day with a sucrose solution to promote a high incidence of dental caries, were treated two times a day with 10 ml of 0.2% chlorhexidine gluconate mouthwash. Inhibition of caries and plaque formation was noted after 22 days. Frequent rinsing with sucrose had been found to produce caries within a 22 day time period (Fehr, F.R. von der, Loc, H., and Theilade, E. 1970. Experimental Caries in Man. Caries Res. 4: 131-148). The authors concluded that "frequent intake of sucrose does not produce caries if the teeth are regularly treated with an antibacterial agent" (Loe, H., Fehr. F. R. von der, and Schiott, C. R. 1972. Inhibition of Experimental Caries by Plaque Prevention. The Effect of Chlorhexidine Mouthrinses Scand. J. Dent. Res.)

Coupled with the problem of identifying antimicrobial compounds effective in reducing dental caries is the necessity that the effective substance may be permitted to act on teeth in the mouth. Thus, not only must the substance possess the requisite effectiveness, it must also possess certain requisite supplementary characteristics, such as satisfactory properties from the viewpoint of oral toxicity, acute chronic toxicity, non-sensitization, etc.

An important feature of this invention is the use of compounds which have low toxicity and which may be readily incorporated into a variety of oral preparations.

SUMMARY OF THE INVENTION

This invention has identified two compositions, pimento berry oil and terpeneless bay oil, known to have some antimicrobial properties, as highly effective antimicrobials against selected cariogenic bacteria. These compounds have the apparent ability to either inhibit the growth of or destroy several highly cariogenic species of streptococci and lactobaccili.

Broadly, the present invention relates to a method for inhibiting cariogenic streptococus mutans, lactobacilli fermenti and casei, oral bacterial responsible for dental plaque, dental caries and combinations of plaque and caries, which method comprises: repeatedly immersing said bacteria in solutions containing, as an active ingredient, an effective amount of a member selected from the group consisting of (a) pimento berry oil, (b) terpeneless bay oil, and (c) combinations of these, until said repeated immersions are effective in inhibiting said bacteria responsible for the formation of dental plaque, dental caries and combinations of plaque and caries.

DETAILED DESCRIPTION

According to the present invention, the active ingredients are employed to repeatedly immerse the bacteria streptococus mutans and lactobacilli fermenti and casei at levels and a frequency effective to inhibit the propagation of these bacteria and, therefore dental plaque and caries for which they are responsible.

By the phrase repeated immersion it is meant that the active ingredient is brought into direct contact with the bacteria and maintained there for a period of time effective when done at effective time intervals between immersions to inhibit the growth of cariogenic bacteria, particularly cariogenic streptococci and cariogenic lactobacilli. The immersion or reimmersion may be achieved by directly swabbing a concentrated solution of the active ingredient onto the teeth where the bacteria reside or by holding it in the mouth in a more dilute solution taken directly or derived from a carrier. The active ingredients can be present in suitably effective amounts in preparations such as toothpaste, tooth powders, mouth washes, or lozenges to provide longer periods of contact with the teeth.

As a number of investigators have found antimicrobials to be effective against dental plaque or caries formation with one to two applications a day, this would appear to be an appropriate regimen for mouthwash or chewing gum use. Since the microbial population of the mouth doubles every 12 to 24 hours, a one or two times a day application would maintain cariogenic organisms only at low levels.

Our nichrome wire experiments indicated that 0.17% pimento berry oil applied for one minute, three times a day for ten days, reduced dextran deposition while a concentration of 0.3% prevented it entirely.

Based on the literature and on our own nichrome wire experiments, we would recommend a regimen for obtaining anticaries and antiplaque activity from chewing gum containing terpeneless bay oil to deliver a level of at least 0.1%. A level of above 0.17% for pimento berry oil would be effective. The preferable levels would be somewhat higher, e.g., above 0.2% for terpeneless bay oil and above 0.25% for pimento berry oil. As a degree of dilution occurs with the saliva as the gum is chewed, a higher level is necessary if gum is the vehicle. The maximum commercial level would, however, be limited by taste. The gum should be chewed from one to three times a day, preferably three times a day. The time for each chewing should be from 2½ to 5 minutes, perferably 5 minutes. Other methods of application could be candy, mouthwash, dentrifice, tooth paint, etc.

The correllation between buildup of plaque and incidence of dental caries is so well established that it is safe to assume that any regimen, which results in reduced plaque formation, will likewise result in formation of fewer dental caries lesions. These regimens would have to be continued as long as cariogenic food (sucrose and other carbohydrate containing food) is consumed. If we use the antimicrobials at bacteriostatic levels, frequent treatment is necessary to prevent buildup of organisms. Even when bactericidal levels are used, constant recolonization of the mouth from crevices in the teeth where the antibiotic has not reached (before it is rendered ineffective by salivary dilution) or by reinoculation from the environment takes place.

Pimento berry oil is a commercially available composition, also known as allspice oil and pimenta oil, is the volatile oil distilled from the fruit of Pimenta Officinalis Lindley (Fam. Myrtaceae). It is used generally as a flavoring material in food products such as chewing gum at levels of up to 0.17% (1700 ppm).

Bay oil is also commercially available and is derived from the leaves of the bay oil tree (pimenta racemosa); usually by distillation as known in the art. It is known to be useful as a flavorant in beverages and food products at levels of from about 1.5 to about 15 ppm.

The terpenes can be removed from the bay oil by fractionation techniques known to the art. For example, the terpenes can be removed by fractional distillation.

Such materials as sweeteners, flavoring, coloring or whitening agents, preservatives, alcohols and the like may be readily incorporated into the oral preparations of this invention. Dentifrice formulations should also contain, as a major proportion of the solid ingredients, water-insoluble abrasives or polishing agents such as calcium carbonate, tricalcium phosphate, bentonite, etc.

In the preparation of tooth powders it is usually sufficient to mechanically blend the various solid ingredients, including effective amounts of the antimicrobial compound and abrasives, into a homogenous powder.

Mouth washes or rinses prepared in accordance with this invention will usually comprise an effective amount of the antimicrobial compound dissolved in a suitably flavored liquid vehicle such as an aqueous alcoholic vehicle.

The lonzenges or troches contemplated by this invention are prepared by mixing particles of the active ingredient with mucilage and natural or artificial sweeteners and flavoring agents. Gelatin and water is also an effective base for these candy-like products. Chewing gum can be prepared by the substitution of a standard gum base for the mucilage. Suitable bulking agents or fillers may be added to any of these edible products.

The oral preparations employed according to this invention may be prepared in accordance with the skill and practice of the prior art. The distinguishing feature of this invention is the inclusion of an effective amount of selected antimicrobial compositions to inhibit the formation of dental plaque and/or reduce the incidence of dental caries. These antimicrobial compositions may be incorporated into the oral preparation either as a substitute for or in addition to other anti-caries agents which have previously been discovered and employed by the prior art.

The antimicrobial compositions or combination of compositions of this invention should be present in the oral preparations in an amount sufficient to produce an effective concentration of the compounds in the mouth. Normally this involves the formation of oral preparations which contain or release the antimicrobial composition in the mouth at a concentration of from about 0.03% to about 1%, preferably from about 0.075% to about 0.75%, and most preferably from about 0.1% to about 0.5%. The percentages being by weight. It will be apparent to those skilled in the art from a reading of this specification that the active ingredients identified according to the present invention will normally be used at lower concentrations when employed with another, complimentary active agent.

EXAMPLE I

The active ingredients of the present invention were tested at various concentrations in a thioglycollate broth medium inoculated with a known amount of cariogenic organism and were quantitatively compared with control cultures which did not contain the antimicrobial compound. Additional cultures containing equivalent amounts of the constituents of pimento berry oil were also investigated but found to be less effective than the pimento berry oil itself as antimicrobials against cariogenic streptococci.

The method of testing consisted of inoculating 5 or 10 ml portions of the thioglycollate broth having added thereto 5% sucrose by weight, a pinch of calcium carbonate and the active ingredient (except control), usually in an ethanol solution. The controls contained like amounts of ethanol. All tests were conducted at 37° C. Counts were determined by plating suitable subdilutions on Mitis Salivarius Agar (Difco).

The results are summarized in the Tables below. Pimento Berry Oil Constituents (the number in parentheses indicate the weight percent of the indicated materials in pimento berry oil):

TABLE I

Inoculum: $2 \times 10^7$ (Strep mutans FA-1; organisms/ml)

| Active Ingredients | Conc. (wt.%) | Count 30 min. | 60 min. | 24 hrs. |
|---|---|---|---|---|
| None | — | $2 \times 10^7$ | $2 \times 10^7$ | $4 \times 10^8$ |
| Eugenol* (69) | 0.1 | $2 \times 10^7$ | $4 \times 10^6$ | $8 \times 10^4$ |
| Pimento Berry Oil | 0.1 | $2 \times 10^6$ | $5 \times 10^5$ | $7 \times 10^3$ |

*also comprises 90% of Bay oil

TABLE II

Inoculum: $3 \times 10^7$ (Strep mutans FA-1; organisms/ml)

| Active Ingredients | Conc. (wt.%) | Count 30 min | 60 min. | 24 hrs. |
|---|---|---|---|---|
| None | — | $4 \times 10^7$ | $4 \times 10^7$ | $5 \times 10^8$ |
| Cineole (2.3) | 0.1% | $2 \times 10^7$ | $3 \times 10^7$ | $9 \times 10^8$ |
| Phellandrine (1.0) | 0.1% | $2 \times 10^7$ | $2 \times 10^7$ | $2 \times 10^7$ |
| Pimento Berry Oil | 0.1% | $8 \times 10^6$ | $9 \times 10^6$ | $7 \times 10^6$ |

TABLE III

Inoculum: $1 \times 10^6$ (Strep mutans FA-1; organisms/ml)

| Active Ingredients | Conc. (wt.%) | Count after 24 hours |
|---|---|---|
| None | — | $2 \times 10^8$ |
| Myrcene (0.8) | 0.1% | $6 \times 10^7$ |
| Terpinolene (0.7) | 0.1% | $6 \times 10^7$ |
| Terpineol (<2.7) | 0.1% | $2 \times 10^8$ |
| P-cymene (1.4) | 0.1% | $6 \times 10^7$ |
| Pimento Berry Oil | 0.1% | $3 \times 10^4$ |

TABLE IV

Inoculum: $3 \times 10^7$ (Strep mutans FA-1; organisms/ml)

| Active Ingredients | Conc. (wt.%) | Count 6 hrs. | 24 hrs. |
|---|---|---|---|
| None | — | $7 \times 10^8$ | $>10^{10}$ |
| Methyl Eugenol (8.8) | 0.1% | $2 \times 10^7$ | $2 \times 10^7$ |
| Eugenol (69) | 0.1% | $9 \times 10^5$ | $9 \times 10^3$ |
| Pimento Berry Oil | 0.1% | $4 \times 10^4$ | $9 \times 10^2$ |

TABLE V

Inoculum: $2 \times 10^7$ (Strep mutans FA-1; organisms/ml)

| Active Ingredients | Conc. (wt.%) | Count 30 min. | 60 min. | 24 hrs. |
|---|---|---|---|---|
| None | 0.1 | $2 \times 10^7$ | $3 \times 10^7$ | $5 \times 10^8$ |
| Eugenol (69) | 0.1 | $2 \times 10^7$ | $4 \times 10^6$ | $8 \times 10^4$ |
| Methyl Eugenol (8.8) | 0.1 | $4 \times 10^7$ | $3 \times 10^7$ | $2 \times 10^8$ |
| Caryophyllene (4.2) | 0.1 | $2 \times 10^7$ | $2 \times 10^7$ | $3 \times 10^8$ |
| Pimento Berry Oil | 0.1 | $3 \times 10^7$ | $5 \times 10^5$ | $7 \times 10^3$ |

TABLE VI

Inoculum: $3 \times 10^7$ (Strep mutans FA-1; organisms/ml)

| Active Ingredients | Conc. (wt.%) | Counts 6 hrs. | 24 hrs. |
|---|---|---|---|
| None | — | $7 \times 10^8$ | $>10^8$ |
| Eugenol (69) | 0.1 | $9 \times 10^5$ | $9 \times 10^3$ |
| Pimento Berry Oil | 0.1 | $4 \times 10^4$ | $9 \times 10^2$ |

Pimento Berry Oil effective against various organisms:

TABLE VII

Inoculum: $7 \times 10^5$ (*L. fermenti*: organisms/ml)

| Active Ingredient | Conc. (wt. %) | Count after 1 hr. |
|---|---|---|
| None | — | $7 \times 10^5$ |
| Pimento Berry Oil | 0.1 | $3 \times 10^2$ |

TABLE VIII

Inoculum: $1 \times 10^6$ (*L. casei*: organisms/ml)

| Active Ingredient | Conc. (wt. %) | Count after 1 hr. |
|---|---|---|
| None | — | $1 \times 10^6$ |
| Pimento Berry Oil | 0.1 | $<10^2$ |

TABLE IX

| Exp. No. | Active Ingredient | Conc. (wt.%) | Original Inoculum (Strep mutans FA-1; organisms/ml) | After 24 hrs. (organisms/ml) |
|---|---|---|---|---|
| 1 | Pimento Berry Oil | 0.1 | $3 \times 10^7$ | $4 \times 10^6$ |
| 2 | Pimento Berry Oil | 0.1 | $8 \times 10^6$ | $2 \times 10^4$ |
| 3 | Pimento Berry Oil | 0.1 | $2 \times 10^7$ | $6 \times 10^2$ |

TABLE X

Inoculum: $4 \times 10^4$ (Strep mutans SL-1; organisms/ml)

| Active Ingredient | Conc. (wt.%) | Count 30 min. | 60 min. |
|---|---|---|---|
| None | 0.1 | $4 \times 10^4$ | $4 \times 10^4$ |
| Pimento Berry Oil | 0.1 | $<10^2$ | $<10^2$ |

TABLE XI

TERPENELESS BAY OIL

Inoculum: $5 \times 10^7$ (*S. mutans* FA-1; organisms/ml)

| Active Ingredient | Conc. (wt.%) | Count 30 min. | 60 min. | 24 hrs. |
|---|---|---|---|---|
| None | — | $6 \times 10^7$ | $5 \times 10^7$ | $4 \times 10^8$ |
| Terpeneless Bay Oil | 0.1 | $5 \times 10^3$ | $9 \times 10^2$ | $<10^2$ |
| Pimento Berry Oil | 0.1 | $3 \times 10^5$ | $3 \times 10^5$ | $1 \times 10^3$ |

TABLE XII

| Active Ingredient | Conc. (wt.%) | Inoculum | S. Mutans Strain | 10 min. | 20 min. |
|---|---|---|---|---|---|
| None | | $3 \times 10^7$ | FA-1 | $3 \times 10^7$ | $3 \times 10^7$ |
| Terpeneless Bay Oil | 0.1 | $3 \times 10^7$ | FA-1 | $3 \times 10^5$ | $2 \times 10^4$ |
| None | | $6 \times 10^7$ | SL-1 | $6 \times 10^7$ | $4 \times 10^7$ |
| Terpeneless Bay Oil | 0.1 | $6 \times 10^7$ | SL-1 | $< 10^2$ | $< 10^2$ |
| None | | $2 \times 10^7$ | E-49 | $2 \times 10^7$ | $2 \times 10^7$ |
| Terpeneless Bay Oil | 0.1 | $2 \times 10^7$ | E-49 | $1 \times 10^5$ | $8 \times 10^3$ |

TABLE XIII

Inoculum: $3 \times 10^7$ (Streptococcus mutans FA-1; organisms/ml)

| Active Ingredient | Conc. Wt.% | 30 min. Count. | 60 min. | 24 hrs. |
|---|---|---|---|---|
| None | — | $7 \times 10^7$ | $6 \times 10^7$ | $4 \times 10^7$ |
| Terpeneless Bay Oil | 0.1 | $5 \times 10^3$ | 900 | 100 |
| Dominican Bay Oil | 0.1 | $7 \times 10^6$ | $4 \times 10^6$ | $4 \times 10^4$ |
| National Formula Bay Oil | 0.1 | $2 \times 10^6$ | $1 \times 10^6$ | $3 \times 10^4$ |

Effect of Terpeneless Bay Oil and Pimento Berry Oil on Lactobacilli:

TABLE XIV

| Active Ingredient | Con. (wt.%) | Inoculum | Lactobacilli Species | 10 min. | 20 min |
|---|---|---|---|---|---|
| None | | $2 \times 10^5$ | L. fermenti | $2 \times 10^5$ | $2 \times 10^5$ |
| Pimento Berry Oil | 0.1 | $2 \times 10^5$ | " | $2 \times 10^2$ | $2 \times 10^2$ |
| Terpeneless Bay Oil | 0.1 | $2 \times 10^5$ | " | $1 \times 10^2$ | $< 10^2$ |
| None | | $1 \times 10^6$ | L. casei | $1 \times 10^6$ | $1 \times 10^6$ |
| Pimento Berry Oil | 0.1 | $1 \times 10^6$ | " | $3 \times 10^2$ | $< 10^2$ |
| Terpeneless Bay Oil | 0.1 | $1 \times 10^6$ | " | $< 10^2$ | $< 10^2$ |

EXAMPLE II

Dextran accumulation by cariogenic strep mutans FA-1 on nichrome wires, and its prevention by Pimento Berry Oil.

A technique has been developed by Jordan & Keyes and others in which cariogenic streptococci deposit dextran on nichrome wires. Usually it takes 10 successive transfers to get a thick coating of dextran. This is what happened in the control wires. The test wires were placed in actively growing cultures of Strep mutans FA-1, removed and immersed three times a day for short periods as given in the Tables XV and XVI in Pimento Berry Oil solutions in thioglycolate broth containing ethanol.

Results may be seen from Tables XV and XVI.

TABLE XV

Treatment 5 minutes, 3 times per day

| Immersion Solution | Deposit after 10 days |
|---|---|
| Control (Saline) | Heavy dextran deposition |
| 5% Ethanol | Heavy dextran deposition |
| 0.17% Pimento Berry Oil + 5% Ethanol | Trace dextran deposition |

TABLE XVI

Treatment 1 minute, 3 times per day

| Immersion Solution | Deposit after 10 days |
|---|---|
| Control (Saline) | Heavy dextran deposition |
| 10% Ethanol | Heavy dextran deposition |
| 0.17% Pimento Berry Oil + 10% Ethanol | Moderate dextran deposition |
| 0.25% Pimento Berry Oil 10% Ethanol | Light dextran deposition |
| 0.30% Pimento Berry Oil + 10% Ethanol | No dextran deposition |

The results show that dilute Pimento Berry Oil solutions severly retarded or completely eliminated dextran formation in this Example, even though contact time and removal from the actively growing culture was only $1 \times 3$ or $5 \times 3$ minutes a day simulating use in normal preparation. It being noted that the ethanol solution by itself gives no noticable improvement.

The above Examples and explanations are for the purpose of teaching those skilled in the art how to practice the present invention. Upon reading this disclosure, those skilled in the art will become aware of a number of modifications and variations. It is contemplated that these modifications and variations be included within the scope of the present invention which is defined by the following claims.

What is claimed is:

1. A method for inhibiting cariogenic streptococcus mutans, lactobacilli fermenti and casei, oral bacteria responsible for the formation of dental plaque, dental caries and mixtures thereof, which comprises reimmersing said bacteria in solutions containing as an active ingredient an amount greater than 0.17% of pimento berry oil, for at least 1 minute, three times each day, until said reimmersions are effective in inhibiting said bacteria responsible for the formation of dental plaque, dental caries and mixtures thereof.

2. A method for inhibiting cariogenic streptococcus mutans, lactobacilli fermenti and casei, oral bacteria responsible for the formation of dental plaque, dental caries and mixtures thereof, which comprises reimmersing said bacteria in solutions containing as an active ingredient an amount greater than 0.1% of terpeneless bay oil, for at least 1 minute, three times each day, until said reimmersions are effective in inhibiting said bacteria responsible for the formation of dental plaque, dental caries and mixtures thereof.

* * * * *